(12) United States Patent
Borkowski

(10) Patent No.: US 6,447,463 B1
(45) Date of Patent: Sep. 10, 2002

(54) HIGHLY SENSITIVE, PRACTICAL, WIDELY AVAILABLE DIAGNOSTIC KIT FOR FUNGAL SKIN INFECTIONS

(76) Inventor: Piotr Borkowski, 3601 NE. 207th St., Suite No. 1104, Aventura, FL (US) 33180

( * ) Notice: Subject to any disclaimer, the term of this patent is extended or adjusted under 35 U.S.C. 154(b) by 66 days.

(21) Appl. No.: 09/708,371

(22) Filed: Nov. 8, 2000

Related U.S. Application Data
(60) Provisional application No. 60/164,478, filed on Nov. 10, 1999.

(51) Int. Cl.[7] .......................... A61B 10/00; A65D 71/00
(52) U.S. Cl. ...................................... 600/562; 206/223
(58) Field of Search .................... 379/265.01; 424/529; 383/113; 600/562, 573, 572; 73/864.21; 604/317, 356, 408, 409, 289; 206/223, 569, 570, 204; 435/6

(56) References Cited

U.S. PATENT DOCUMENTS

| | | | |
|---|---|---|---|
| 4,122,947 A | 10/1978 | Falla .......................... 206/569 |
| 4,886,071 A | 12/1989 | Mehl et al. .................. 128/760 |
| 4,949,840 A * | 8/1990 | Brown ........................ 206/204 |
| 5,025,920 A * | 6/1991 | Walsh et al. ................. 206/223 |
| 5,156,948 A | 10/1992 | Christensen et al. ........... 435/5 |
| 5,190,049 A * | 3/1993 | Briggs et al. ................ 600/573 |
| 5,199,795 A * | 4/1993 | Russo et al. ................. 383/113 |
| 5,211,286 A * | 5/1993 | Turner ........................ 206/223 |
| 5,470,323 A * | 11/1995 | Smith et al. .................. 604/289 |
| 5,769,794 A * | 6/1998 | Conlan et al. ............... 600/562 |
| 5,921,396 A * | 7/1999 | Brown, Jr. ................... 206/569 |
| 6,106,732 A | 8/2000 | Johnston et al. ............. 210/767 |
| 6,176,836 B1 * | 1/2001 | Trudil et al. ................. 600/572 |
| 6,226,378 B1 | 5/2001 | Quattrocchi ................. 379/265 |
| 6,291,171 B1 * | 9/2001 | Ricciardi et al. ............... 435/6 |
| 6,300,140 B1 | 10/2001 | Robinson et al. ........... 436/518 |

OTHER PUBLICATIONS

Though not prior art, Applicant notes for record that he has a co-pending application (09/708,318) also having a filing date of Nov. 8, 2000.

* cited by examiner

Primary Examiner—Eric F. Winakur
Assistant Examiner—Nikita R Veniaminov
(74) Attorney, Agent, or Firm—Malin, Haley & DiMaggio, P.A.

(57) ABSTRACT

A fungal skin infection diagnostic kit is disclosed with a plurality of components stored within a box. The box can be provided with a colorful, attractive front graphic and may include a photo of a working pathologist, etc. The box can be provided with a hole allowing for easy hanging and display of the product. The kit is used for transferring one or more skin legions to a remote location, such as a diagnostic lab. The kit can include a plastic diagnostic slide with attached self-adhesive tape, a plastic specimen bag where the slide with attached skin legion can be placed, medical information and use instructions, and a return envelope. The specimen bag is preferably provided with a zip-type closing mechanism and a bar code with corresponding case number. The return envelope is preferably prepaid. The kit can also include a data form to be filled out by the user for his or her personal information.

20 Claims, 4 Drawing Sheets

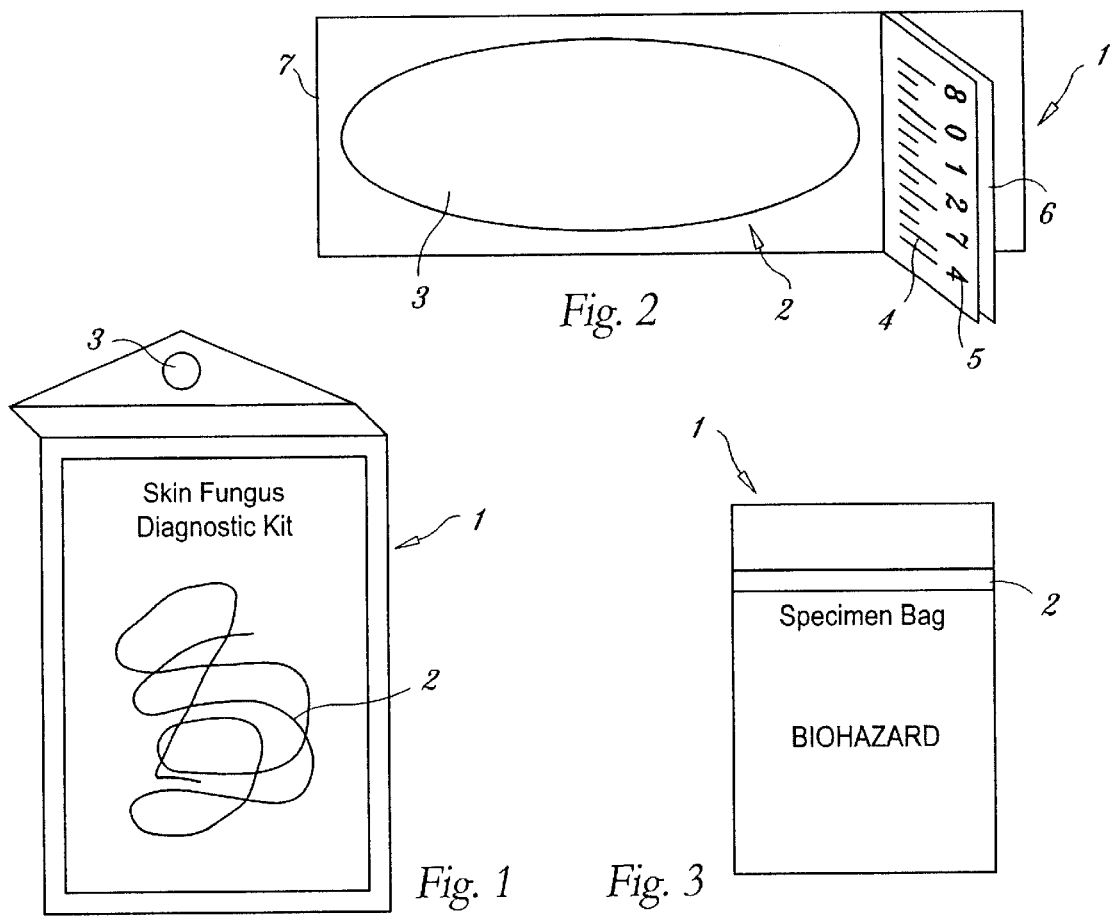
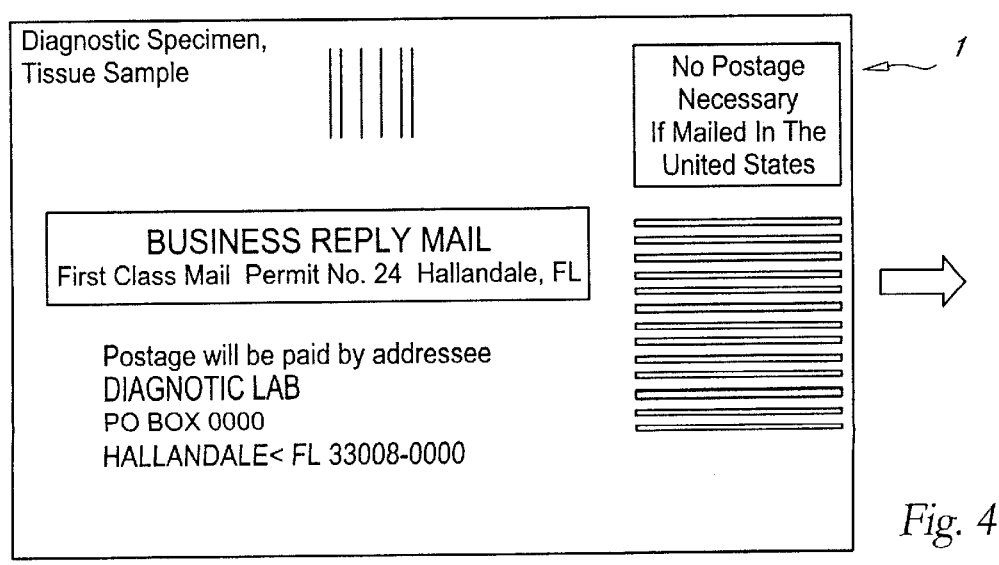

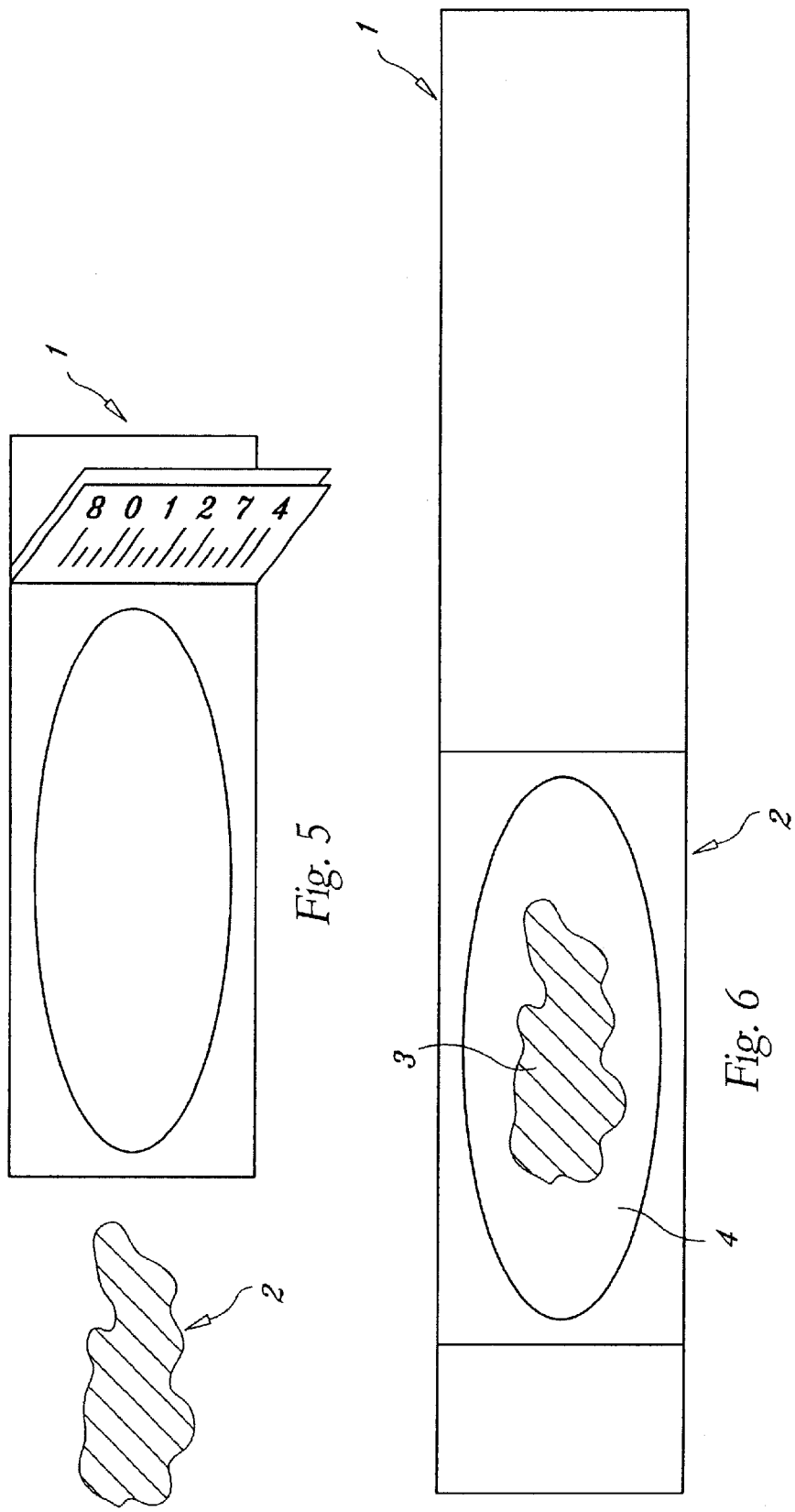

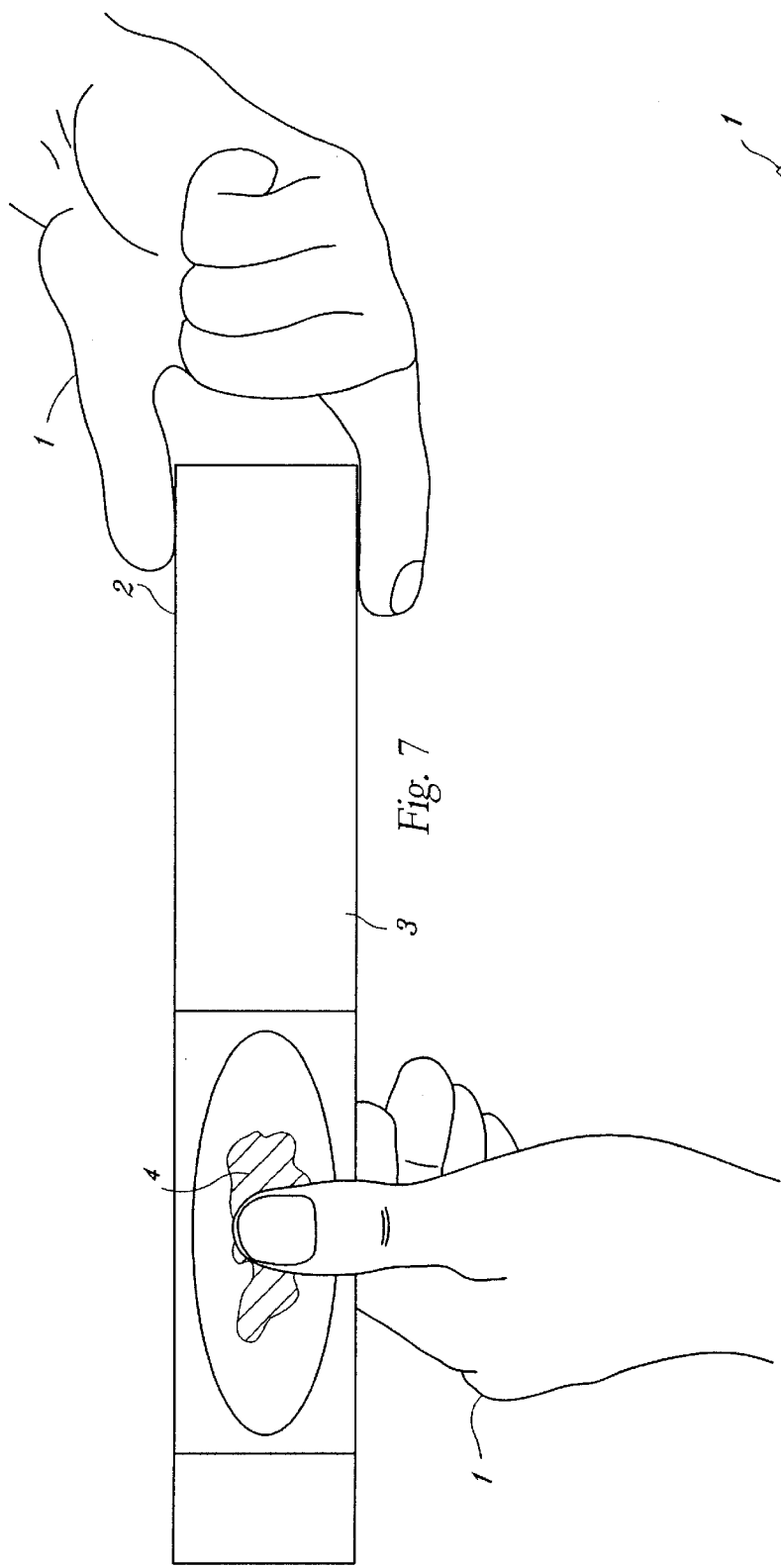
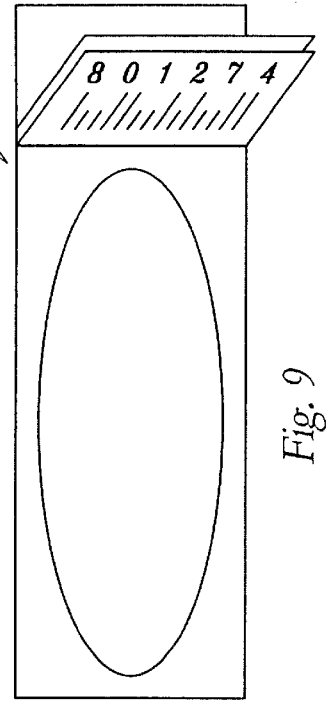
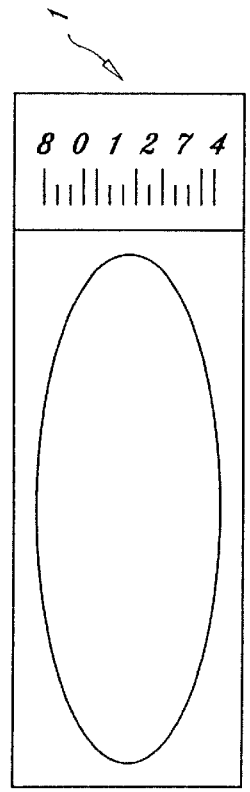

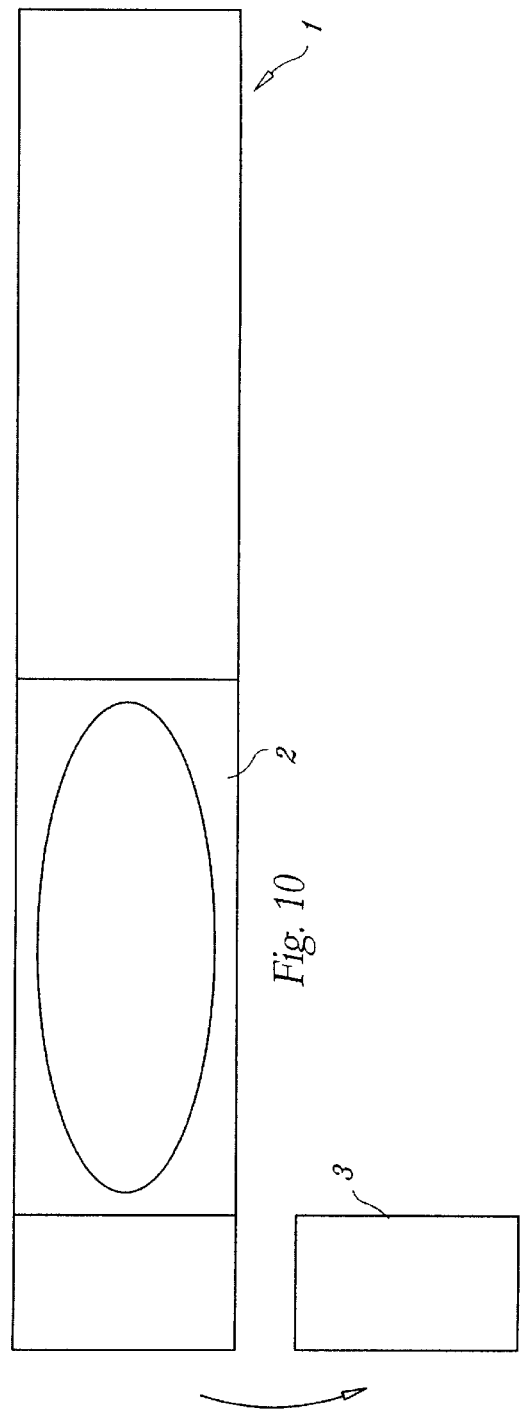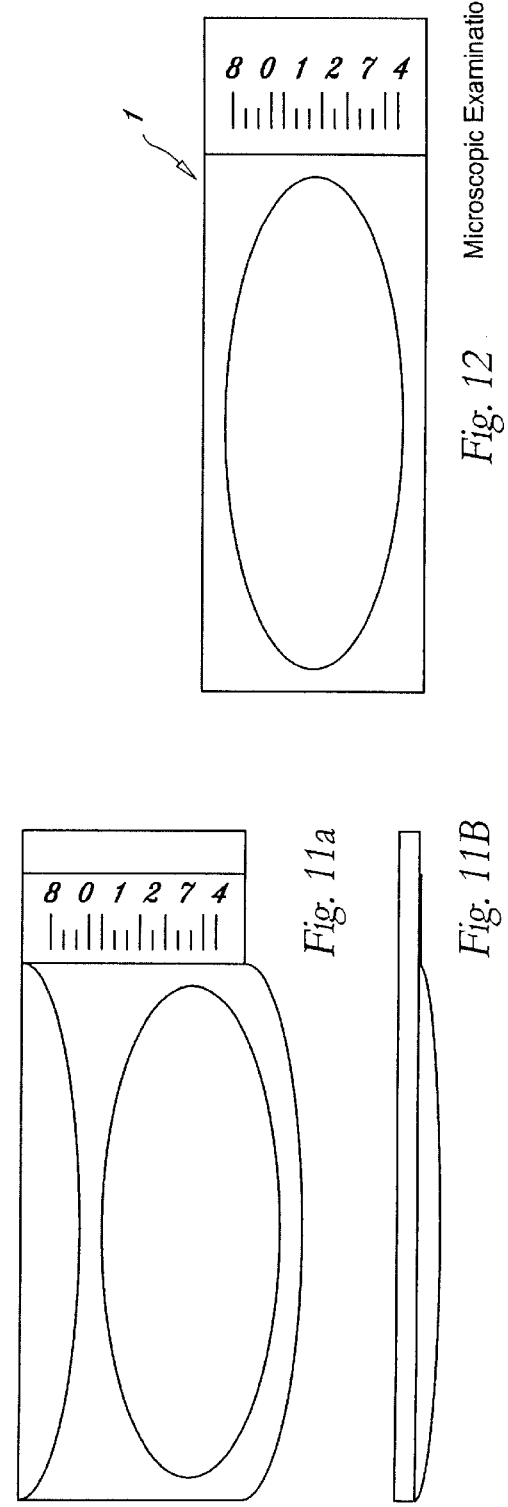

HIGHLY SENSITIVE, PRACTICAL, WIDELY AVAILABLE DIAGNOSTIC KIT FOR FUNGAL SKIN INFECTIONS The present invention claims priority to and the benefit of U.S. Provisional Application No. 60/164,478, filed Nov. 10, 1999.

BACKGROUND OF THE INVENTION

1. Field of Invention

The present invention relates to a very sensitive, practical, useful, widely available diagnostic kit for fungal skin infections.

2. Background—Description of Art

Fungal skin infection is a common medical problem worldwide. In the United States, one of every five persons gets a fungal infection at some time. Athlete's foot (tinea pedis) is the most common fungal skin infection. It affects approximately 70 percent of adult population. Many people, especially teenagers and young men will acquire it at least once in a lifetime. Factors predisposing to athlete's foot include heavy sweating, not drying feet after bathing, warm and moist climate, heavy-duty athletic activities and tight shoes and socks, especially made of synthetic materials. Other fungal skin diseases may involve the groin area (jock itch), underarms, legs, face and chest and back (tinea versicolor). Fungal infections of the skin may manifest as skin discoloration (pale, dark, red patches), itching, burning, pain and discomfort. The skin can become brittle and scaling can occur. Occasionally the skin can develop fissures, blisters and ulcers followed by scarring. Infections, if left untreated, may lead to cellulitis, sever pain and discomfort and even to systemic dissemination of the disease. Especially serious problems may be encountered in diabetic and immunocompromised patients. Offensive clinical presentation of the disease can also lead to social stigma with negative effect on self-esteem and social interaction.

A firm, definite diagnosis of fungal skin diseases is crucial before prescribing antifungal agents. All medications carry a potential risk for toxic reactions and drug interactions and many medications are costly. The list of diagnostic tools for fungal skin diseases in a clinical setting includes potassium hydroxide (KOH) preparation, fungal cultures and surgical pathology diagnostic tests. KOH preparation appears to serve as a most commonly utilized diagnostic test followed by cultures. Both KOH and surgical pathology diagnostic tests involve scraping of the superficial layer of skin with scalpel or glass slide edge. This procedure is considered invasive and has to be performed in doctor's office by a trained medical practitioner.

In KOH preparation, the specimen is placed on a microscopic slide, softened by 20% KOH, and heated under a heat source. The specimen is then evaluated microscopically for the presence of fungal elements (yeasts and hyphae). In surgical pathology diagnostic test the skin scrapings are stained with periodic acid-Schiff reaction (PAS) and also examined under microscope. In fungal cultures, the specimen is usually placed on dermatophyte test and Sabouraud dextrose agar media. Cultures are allowed four weeks to grow. At the end of this period, fungal samples are removed from the media, stained with lactophenol blue, and examined microscopically for the identification of specific genus and species. Unfortunately cultures can take as long as a month to grow and approximately 30–40% of cultures may be negative.

Interestingly, in fungal skin infections, the usual location of the causative fungus is in the outermost layer of the skin. This layer is called cornified layer or stratum cornum. This part of the skin is dead and easily detachable. The cell from the cornified layer are constantly slough in a natural process. I made an observation that these cells can even be easily lifted with a self adhesive tape like Scotch tape®. This fact led me to create an idea of highly sensitive, useful, non-invasive, widely available diagnostic kit for fungal skin infections.

SUMMARY OF THE INVENTION

The objectives of the proposed invention are to provide the general public, cosmetologists and health care providers (podiatrists, dermatologists, family practitioners, physical therapists, internists, orthopedists, etc) with a simple, highly sensitive, useful, practical, non-invasive, safe, informative, widely available, and inexpensive diagnostic kit for fungal skin infection.

The basis of the invention is the usual location of pathogenic fungi within dead, easily detachable outermost layer of the skin. The invention is also based on superior sensitivity and usefulness of histochemical PAS stain in tissue preparations. The Diagnostic Test Kit for fungal skin diseases can include colorful, attractive packaging (FIG. 1). The kit can also include a translucent, plastic diagnostic slide with retractable, self adhesive, centrally translucent tape (FIG. 2). The kit will also contain a plastic, zip-lock type, biohazard specimen bag (FIG. 3) and a return, prepaid envelope (FIG. 4). The kit can include medical information about fungal skin infections and use an instruction booklet. Each kit can have a specific computerized identification number. The user or customer, such as a person with suspicious looking skin changes (e.g. discolored, thickened, fissured, cracked, peeling, itching skin), will preferably be able to purchase the kit in the drug stores, grocery stores, health oriented stores, beauty salons, health salons, doctors offices, etc. The customer can be able to become familiar with medical aspects of fungal skin infections from the medical information booklet. The instructions booklet can specify how to obtain diagnostic sample of cornified layer of the skin using provided plastic slide with attached adhesive tape. (FIG. 2). The suspicious area of the skin can be touched with adhesive part of the tape. The customer can be instructed to reattached the tape to the plastic slide, place the slide in the specimen bag and mail the sample to the skin fungus diagnostic lab using provided prepaid envelope. In the laboratory the slide and the tape can be partially detached and stained with PAS stain. A pathologist can read the slide and make the diagnosis for presence or absence of fungal skin infection. A written result report can be faxed/mailed to the clinician in charge of the patient/customer or send to the computerized, telephone or Internet report system. The customer can then have the opportunity to obtain the diagnosis and medical recommendation message over the phone (or internet) using his identification number. The specimen processing system offers opportunity for potential automatization. Trained technicians could also prescreen the slides.

BRIEF DESCRIPTION OF THE DRAWINGS

FIG. 1 is a front perspective view of the Fungal Skin Infections Diagnostic Kit box;

FIG. 2 illustrates plastic diagnostic slide with attached self-adhesive tape;

FIG. 3 is a front perspective view of a plastic specimen bag;

FIG. 4 is a front perspective view of a prepaid return envelope;

FIG. 5 is a front perspective view of the plastic diagnostic slide with attached self-adhesive tape and a view of a fungal skin lesion;

FIG. 6 is a front perspective view of a plastic diagnostic slide with an opened self-adhesive tape and a view of the fungal skin lesion located behind the tape central translucent window;

FIG. 7 illustrates clinician's (or customer's) hands holding the diagnostic slide and gently pressing the adhesive tape against easily visible skin lesion;

FIG. 8 is a front perspective view of the plastic diagnostic slide with reattached adhesive tape;

FIG. 9 is a front perspective view of the plastic diagnostic slide with attached self-adhesive tape received in the lab;

FIG. 10 is a front perspective view of the plastic diagnostic slide with partially detached self-adhesive tape receive in the lab;

FIG. 11 is a front (3*a*) and side (3*b*) perspective view of a plastic diagnostic slide with a slightly detached self-adhesive tape for staining with PAS; and FIG. 12 is a front perspective view of a stained plastic diagnostic slide with reattached adhesive tape ready for microscopic examination.

DETAILED DESCRIPTION OF THE INVENTION

Referring to FIG. 1, Fungal Skin Infections Diagnostic Kit box 1 has a colorful, attractive front graphic 2 that may include a photo of working pathologist etc. The box can be provided with a hole 3 allowing easy hanging and display of the product. As illustrated in FIG. 2 the kit can include a plastic diagnostic slide 1 with attached self-adhesive tape 2. The adhesive tape preferably has a translucent window 3, bar code 4, corresponding to bar code number 5 and rectangular piece of glossy paper 6 attached to the back of a free end of adhesive tape. Alternatively or additionally, the bar code and/or bar code number can also be provided on the specimen bag. The other end of the tape is preferably attached permanently to the edge 7 of plastic slide.

In lieu of the self adhesive tape, other non-intrusive, non-traumatic removal means can be used and all are considered within the scope of the invention. One alternative can be a sponge or sponge-like member. Other devices which allow for easy access to and removal of the outermost layer of the individuals skin are also within the scope of the invention.

FIG. 3 shows a plastic specimen bag 1 where the plastic diagnostic slide will be placed. The bag has a zip-type closing mechanism 2. In FIG. 4 prepaid return envelope 1 shows typical U.S. postal service specification elements. The type of used envelopes should be of good quality, plastic lined, tight and easily self sealed for added safety and security.

FIG. 5 shows a plastic diagnostic slide 1 described above. It also shows a simplified drawing of a fungal skin lesion 2. FIG. 6 shows a plastic diagnostic slide 1 with an opened self adhesive tape 2 and a view of the fungal skin lesion 3 located behind the tape central translucent window 4. FIG. 7 illustrates clinician's (or customer's) hands 1 holding the diagnostic slide 2 and gently pressing the adhesive tape 3 against easily visible skin lesion 4. FIG. 8 shows plastic diagnostic slide with reattached adhesive tape.

FIG. 9 shows a plastic diagnostic slide as received in a Skin Fungus Diagnostic Lab. FIG. 10 illustrates plastic diagnostic slide 1 with an opened self-adhesive tape 2 and removed rectangular piece of glossy paper 3. FIG. 11 shows a front (3*a*) and side (3*b*) perspective view of a plastic diagnostic slide with a slightly detached self-adhesive tape for staining with PAS. This detachment allows chemicals to react with fungal elements attached together with dead squamous cells of the skin to the adhesive tape. FIG. 12 shows a plastic diagnostic slide with reattached adhesive tape for microscopic examination.

The kit can also include a data form to be filled out by the user. The form can request information concerning how long the skin has been infected, personal data on the customer, color of skin, other description of the skin (i.e. flaky, friable, etc.), any previous conditions, age, sex, insurance information, whether skin legion is causing pain, whether skin is infected, etc. Other information is also within the scope of the invention.

Preliminary Experiment

Preliminary experiment involved a single patient with multiple fungal skin infection lesions located on his chest and back (tinea versicolor). The skin lesions presented as multiple, pale patches ranging in size from 3 cm to 0.3 cm in greatest dimension. The lesions were not painful, however cosmetically unpleasant. Ten (10) lesions were selected randomly. Each lesion was touched with a piece of a Scotch tape®. The tape fragments were than attached to glass slides and stained with PAS. All slides were positive for fungal hyphae, a diagnostic finding of fungal skin infection. Identical experiment was repeated with a healthy person as a control. All ten (10) control slides were negative. Although broad studies will be necessary for statistically significant conclusions, the above experiment is strongly supportive of the idea of a highly sensitive, practical, widely available diagnostic kit for fungal skin infections.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A kit for transferring superficial skin lesions to a remote location for diagnostic testing for fungal skin infections, said kit comprising:

a specimen bag defining a receiving area for storage of the skin lesion to be analyzed;

means for non-intrusive removal of a superficial skin lesion from an individuals body; and an envelope containing the address of the remote location, said specimen bag having said skin lesion stored within said receiving area disposed within said envelope when mailing said envelope to the remote location.

2. The kit of claim 1 wherein said envelope is a return, prepaid envelope.

3. The kit of claim 1 further including medical information regarding fungal skin infections and use instructions.

4. The kit of claim 1 further including means for storing said envelope, said means for non-intrusive removal and said specimen bag prior to use.

5. The kit of claim 4 wherein said means for storing is a box-like member, said envelope, said means for non-intrusive removal and said specimen bag contained within said box-like member prior to use.

6. The kit of claim 1 wherein said means for non-intrusive removal is a slide with attached self-adhesive tape.

7. The kit of claim 1 wherein said specimen bag is a biohazard bag having a zip-lock type closure mechanism.

8. The kit of claim 1, said means for non-intrusive removal having a specific identification number.

9. The kit of claim 8 wherein said specific identification number is a bar code and corresponding case number.

10. The kit of claim 1 further including a data form for filling out by a user.

11. A kit for transferring skin lesion to a remote location for diagnostic testing for fungal skin infections, said kit comprising:
   a biohazard specimen bag defining a receiving area for storage of the skin lesion to be analyzed;
   medical information regarding fungal skin infections and use instructions;
   means for non-intrusive removal of a superficial skin lesion from an individual's body, said means for non-intrusive removal having a specific bar code and corresponding case number;
   a data form for filling out by a user;
   a return, prepaid envelope containing the address of the remote location, said specimen bag having said skin lesion stored within said receiving area disposed within said envelope when mailing said envelope to the remote location; and
   means for storing said medical information, said instructions, said means for non-intrusive removal, said data form, said envelope and said specimen bag prior to use.

12. The kit of claim 11 wherein said means for storing is a box-like member, said medical information, said instructions, said means for non-intrusive removal, said data form, said envelope and said specimen bag contained within said box-like member prior to use.

13. The kit of claim 11 wherein said means for non-intrusive removal is a plastic slide with attached self-adhesive tape.

14. The kit of claim 11, said specimen bag having a zip-lock type closure mechanism.

15. A method for transferring a skin lesion to a remote location for diagnostic testing for fungal skin infections, said method comprising the steps of:
   (a) removing a skin lesion from its attachment to an individual;
   (b) placing said skin lesion in a specimen bag;
   (c) placing the specimen bag in a envelope; and
   (d) mailing the envelope to a remote location.

16. The method for transferring a skin lesion claim 15 further comprising the step of closing said specimen bag by zip-lock type closure once said skin lesion is placed within said specimen bag.

17. The method for transferring a skin lesion of claim 15 further including the step of filling out a data form about the individual and inserting the data form within the envelope prior to mailing the envelope to the remote location.

18. The method for transferring a skin lesion of claim 15 wherein step (a) comprises contacting an outermost skin layer of the individual associated with the skin lesion with a self-adhesive tape and attaching said tape with skin lesion to a slide.

19. The method for transferring a skin lesion of claim 18 wherein step (b) comprises inserting the slide with attached skin lesion within the specimen bag.

20. A method for testing a skin lesion for fungal skin infections, said skin lesion provided on a self-adhesive tape, said self-adhesive tape attached to a slide, said self-adhesive tape having a first end and a second end, said self-adhesive tape having a removal tab at its second end, said tab covering an adhesive area at the second end of said slide, said method comprising the steps of:
   (a) opening said slide such that the self-adhesive tape is only attached at its first end to side slide;
   (b) removing said tab to expose the adhesive portion of the second end of said self-adhesive tape;
   (c) attaching the second end of said self-adhesive tape to the slide to form a gap between said self-adhesive tape and said slide; and
   (d) providing chemicals on the skin lesion through the gap.

* * * * *